United States Patent

Rempfler

Patent Number: 5,500,407
Date of Patent: Mar. 19, 1996

[54] TRIAZOLOPYRIMIDINE HERBICIDES

[75] Inventor: Hermann Rempfler, Ettingen, Switzerland

[73] Assignee: Ciba-Geigy Corporation, Tarrytown, N.Y.

[21] Appl. No.: 341,586

[22] PCT Filed: Mar. 14, 1994

[86] PCT No.: PCT/EP94/00778
§ 371 Date: Nov. 21, 1994
§ 102(e) Date: Nov. 21, 1994

[87] PCT Pub. No.: WO94/21640
PCT Pub. Date: Sep. 29, 1994

[30] Foreign Application Priority Data

Mar. 25, 1993 [CH] Switzerland ............ 907/93

[51] Int. Cl.⁶ .................. C07D 487/04; A01N 43/90
[52] U.S. Cl. .................. 504/241; 544/263; 549/446
[58] Field of Search ............ 504/241; 544/263; 549/434, 446

[56] References Cited

PUBLICATIONS

Hauser et al., Alkaline Cleavage of Unsymmetrical β–Diketones, J. Am. Chem. Soc. vol. 70, pp. 4023–4026 (1948).
β–Diketones from Methyl Alkyl Ketones, Organic Synthesis, vol. 51, pp. 90–93 (1971).
Treibs et al., Synthesen mit Acetessigsavres tert.–butylester, Chem. Ber., No. 87, pp. 1163–1166 (1954) plus English Abstract (1954).
Abdulla et al., An Efficient Conversion of Ketones to α,β–Unsaturated Ketones, J. Org. Chem., vol. 43, No. 21, pp. 4248–4250 (1978).
English Translations of Lopyrev et al., Ahurnal Obshchei Khimii, vol. 53, No. 7, p. 1684 (1983).
Hauser et al., The Acylation of Ketones to form β–Diketones or β–Keto Aldehydes, Organic Reactions, vol. VIII, pp. 59–63 (1954).
Temple, Jr., The Chemistry of Heterocyclic Compounds, vol. 37, cover page and table of contents (1981).

Primary Examiner—Donald G. Daus
Attorney, Agent, or Firm—Marla J. Mathias; William A. Teoli, Jr.

[57] ABSTRACT

Triazolo pyrimidines of the formula

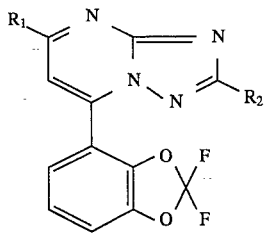

wherein $R_1$ is hydrogen, $C_1$–$C_4$alkyl or $C_1$–$C_4$haloalkyl; and $R_2$ is $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkoxy-$C_1$–$C_4$alkyl, $C_1$–$C_4$-alkoxy-$C_1$–$C_4$alkoxy, $C_1$–$C_4$alkoxy-$C_1$–$C_4$alkylthio, halogen, amino, $C_1$–$C_4$alkylamino or $C_1$–$C_4$dialkylamino, have pre- and postemergence herbicidal properties. Their preparation use thereof as herbicides are described.

20 Claims, No Drawings

TRIAZOLOPYRIMIDINE HERBICIDES

"This is a Section 371 filing of PCT/EP94/00778 filed Mar. 14, 1994, published as WO 94/21640".

The present invention relates to novel herbicidally active triazolopyrimidines, to their preparation, to compositions containing said compounds as active ingredients, and to the use thereof for controlling weeds, especially in crops of cultivated plants or for inhibiting plant growth.

Herbicidally active triazolopyrimidines are known and disclosed, inter alia, in WO 90/12012 and U.S. Pat. No. 4,209,621.

Novel triazolopyrimidines having herbicidal and growth-regulating properties have now been found.

Accordingly, the invention relates to compounds of formula I

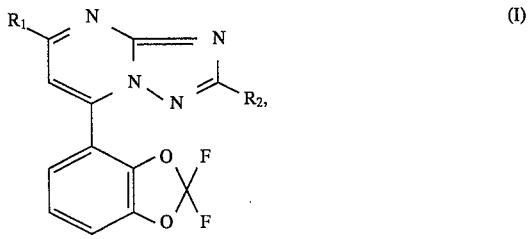

wherein
$R_1$ is hydrogen, $C_1$–$C_4$alkyl or $C_1$–$C_4$haloalkyl; and
$R_2$ is $C_1$–$C_4$alkyl, $C_1$–$C_4$haloalkyl, $C_1$–$C_4$alkoxy, $C_1$–$C_4$haloalkoxy, $C_1$–$C_4$alkylthio,
$C_1$–$C_4$haloalkylthio, $C_1$–$C_4$alkoxy-$C_1$–$C_4$alkyl, $C_1$–$C_4$alkoxy-$C_1$–$C_4$alkoxy, $C_1$–$C_4$alkoxy-$C_1$–$C_4$alkylthio, halogen, amino, $C_1$–$C_4$alkylamino or $C_1$–$C_4$ dialkylamino.

Halogen substituents in the above definitions will be taken to mean fluoro or iodo, and preferably chloro and bromo.

The alkyl groups occurring in the definitions of the substituents may be straight-chain or branched and are typically methyl, ethyl, n-propyl, isopropyl, n-butyl, sec-butyl, isobutyl or tert-butyl. Methyl and ethyl are preferred. Such structural units may also occur in the following substituents.

Haloalkyl will conveniently be alkyl groups that carry one or more, preferably one to five, identical or different halogen substituents, said halogen substituents being bromo or iodo and, preferably, fluoro and chloro. Illustrative examples of such groups are difluoromethyl, chlorodifluoromethyl, trifluoromethyl, pentafluoroethyl, 1,1-dichloro-2,2,2-trifluoroethyl, 2,2,2-trifluoroethyl and 1,1,2,2-tetrafluoroethyl.

Alkoxy is typically methoxy, ethoxy, propoxy, isopropoxy, n-butoxy, isobutoxy, sec-butoxy or tert-butoxy. Methoxy and ethoxy are preferred.

Haloalkoxy is exemplified by difluoromethoxy, trifluoromethoxy, 2,2,2-trifluoroethoxy or 1,1,2,2-tetrafluoroethoxy.

Alkylthio is typically methylthio, ethylthio, n-propylthio, isopropylthio, n-butylthio, isobutylthio, sec-butylthio or tert-butylthio. Methylthio is preferred.

Haloalkylthio will typically be difluoromethylthio, trifluoromethylthio, 2,2,2-trifluoroethylthio or 1,1,2,2-tetrafluoroethylthio. Difluoromethylthio and trifluoromethylthio are preferred.

Alkoxyalkoxy will typically be methoxymethoxy, methoxyethoxy, ethoxymethoxy, ethoxyethoxy and propoxymethoxy. Methoxymethoxy is preferred.

Alkoxyalkyl is typically methoxymethyl, methoxyethyl, ethoxymethyl or ethoxyethyl. Methoxymethyl is preferred.

Alkylamino is typically methylamino, ethylamino, n-propylamino or isopropylamino. Methylamino is preferred.

Dialkylamino is exemplified by dimethylamino, methylethylamino, diethylamino or n-propylmethylamino. Dimethylamino is preferred.

In preferred compounds of formula I, $R_1$ is hydrogen or $C_1$–$C_4$alkyl. Among this group of compounds, those compounds are particularly preferred in which $R_1$ is hydrogen, methyl or ethyl.

Preferred compounds of formula I are also those wherein $R_1$ is methyl and $R_2$ is as defined for formula I. Among this group of compounds, those compounds are especially preferred in which $R_2$ is trifluoromethyl or $C_1$–$C_4$haloalkoxy.

Further preferred compounds of formula I are those wherein $R_2$ is $C_1$–$C_4$alkyl, $C_1$–$C_4$haloalkyl, $C_1$–$C_4$alkoxy, $C_1$–$C_4$haloalkoxy, halogen, amino, $C_1$–$C_4$alkylamino or $C_1$–$C_4$dialkylamino.

Among this group of compounds, those compounds of formula I are particularly preferred wherein $R_2$ is $C_1$–$C_2$alkyl, $C_1$–$C_2$haloalkyl, $C_1$–$C_2$alkoxy, $C_1$–$C_2$haloalkoxy, chloro, bromo, amino, methylamino or dimethylamino. Among this group of compounds, those compounds are in turn especially preferred in which $R_2$ is $C_1$–$C_2$haloalkyl, $C_1$–$C_2$haloalkoxy or amino.

Important compounds of formula I are also those wherein $R_2$ is $C_1$–$C_4$alkylthio, $C_1$–$C_4$haloalkylthio or $C_1$–$C_4$alkoxy-$C_1$–$C_4$alkoxy. Among this group of compounds, those compounds of formula I are of especial importance wherein $R_2$ is $C_1$–$C_2$alkylthio, $C_1$–$C_2$haloalkylthio or $C_1$–$C_2$alkoxy-$C_1$–$C_2$alkoxy.

A further group of preferred compounds of formula I comprises those compounds wherein $R_1$ is hydrogen, $C_1$–$C_2$alkyl or trifluoromethyl; and $R_2$ is $C_1$–$C_2$haloalkyl, $C_1$–$C_2$haloalkoxy or amino. Among this group of compounds, those compounds are very particularly preferred wherein $R_2$ is trifluoromethyl or $C_1$–$C_4$haloalkoxy.

Preferred compounds are also those wherein $R_1$ is hydrogen, methyl, ethyl or trifluormethyl; and $R_2$ is methyl, methoxy, methoxymethoxy, chloro, bromo, trifluoromethyl, difluoromethyl, chlorodifluoromethyl, pentafluoroethyl, 1,1-dichloro-2,2,2-trifluoroethyl, difluoromethoxy, 2,2,2-trifluoroethoxy, 1,1,2,2-tetrafluoroethoxy, methylthio, difluoromethylthio, trifluoromethylthio, amino, methylamino or dimethylamino.

The process of this invention for the preparation of the compounds of formula I is carried out in general accordance with known processes and comprises a) to prepare triazolopyrimidines of formula I, wherein $R_1$ is $C_1$–$C_4$alkyl or $C_1$–$C_4$haloalkyl and $R_2$ is as defined for formula I, reacting a compound of formula II

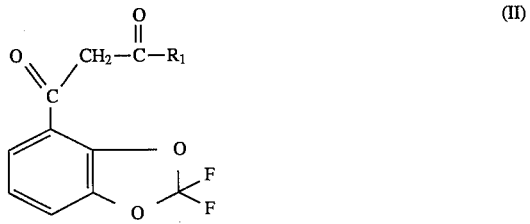

with a compound of formula III

in which compounds of formulae II and III $R_1$ and $R_2$ have the given meanings, without a solvent or in an inert, polar protic or aprotic solvent, in the temperature range from 50° to 150° C. or the boiling temperature of the solvent employed;

b) to prepare triazolopyrimidines of formula I, wherein $R_1$ is hydrogen and $R_2$ is as defined for formula I, reacting a compound of formula IV

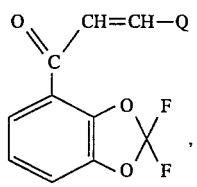     (IV)

wherein Q is a suitable leaving group such as dialkylamino, alicyclic amino, alkylthio or alkoxy, preferably dimethylamino, morpholino, methylthio or methoxy, with a compound of formula III

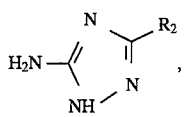     (III)

wherein $R_2$ has the given meaning, without a solvent or in an inert, polar protic or aprotic solvent and in the temperature range from 50° to 150° C. or the boiling temperature of the solvent employed.

The two process variants a) and b) are carried out in accordance with reaction scheme 1.

Reaction scheme 1:

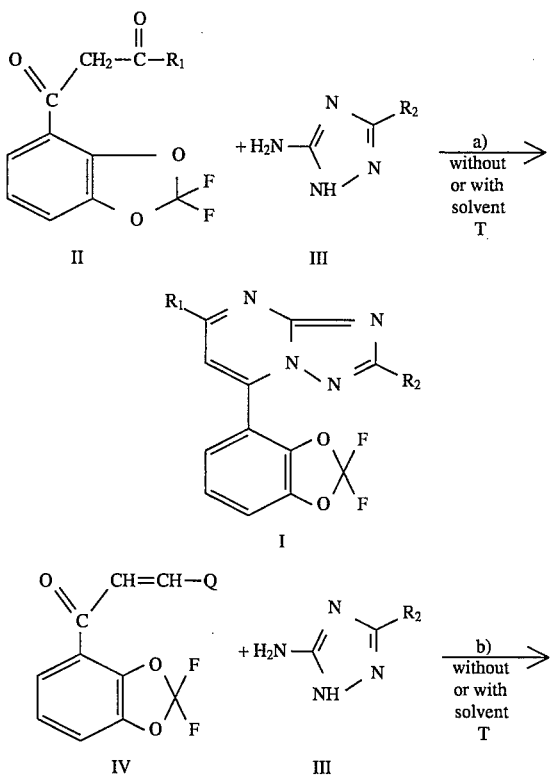

Reaction scheme 1:
-continued

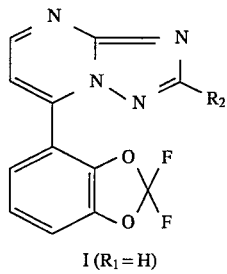

I ($R_1$ = H)

Process variant a), which is suitable for the synthesis of triazolopyrimidine derivatives of formula I, wherein the substituent $R_1$ is $C_1$–$C_4$alkyl or $C_1$–$C_4$haloalkyl and $R_2$ is as defined for formula I, may conveniently be carried out by heating the compound of formula II either without a solvent or in the presence of an inert, polar protic or aprotic solvent, together with the aminotriazole of formula III for 0.5 to 12 hours, preferably for 1 to 6 hours. Suitable solvents are typically glacial acetic acid, ethanol, methanol, dimethyl formamide and dimethyl sulfoxide. The reaction temperatures are preferably in the range from 50° to 150° C. or the boiling temperature of the solvent employed. The regioisomeric product of formula Ia

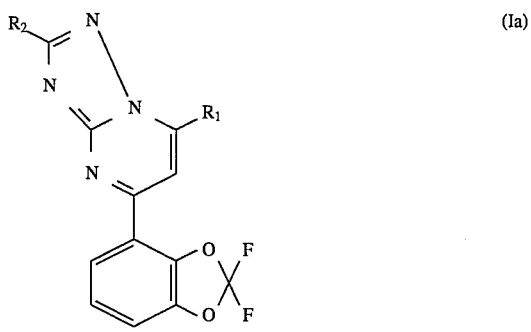     (Ia)

can also be obtained as by-product in c. 5–10 % yield (depending on the reaction conditions).

Process variant b), which is suitable for the synthesis of triazolopyrimidine derivatives of formula I containing an unsubstituted pyrimidine ring ($R_1$=H) and a radical $R_2$ as defined in connection with formula I, may conveniently be carried out by heating the compound of formula III either without a solvent or in the presence of an inert, polar protic or aprotic solvent, together with the compound of formula IV. Suitable solvents are typically glacial acetic acid, ethanol, methanol, dimethyl formamide and dimethyl sulfoxide. The temperature range is from 50° to 150° C. or the boiling temperature of the solvent employed.

The final products of formula I can be isolated in conventional manner by concentrating the reaction mixture and/or removing the solvent by evaporation, and by recrystallising or triturating the solid residue in a solvent in which it is not readily soluble, typically an ether, an aromatic hydrocarbon or a chlorinated hydrocarbon, or by column chromatography.

The intermediates of formulae II and IV are novel and have been specially developed for the synthesis of the compounds of formula I. They therefore also constitute an object of this invention.

The novel β-diketones of formula II can be prepared by different standard procedures known from the literature (e.g. Claisen acylation), as described, inter alia, in Organic Reactions, Volume VIII, page 59 et seq., John Wiley & Sons, 1954; Organic Synthesis 51, 90(1971); J. Am. Chem. Soc. 67, 284 (1945); ibid. 68, 2742 (1946); ibid. 70, 4023 (1948); and in Organikum, page 579, VEB Deutscher Verlag der Wissenschaften, 15th Edition, Berlin 1976. A suitable route of synthesis is illustrated e.g. in reaction scheme 2. According to this scheme, the tert-butyl acylacetate of formula VI is reacted under basic conditions with the benzoyl chloride of formula V in a first reaction step, and, in a second step, the tert-butyl diketoacetate obtained as intermediate is converted by acid catalysis into the desired β-diketone of formula II in accordance with Chem. Ber. 87, 1163 (1954).

(1978). Suitable routes of synthesis are illustrated in e.g. reaction scheme 3. According to this reaction scheme, the acetophenone derivative of formula VIII is reacted with N,N-dimethylformamide dimethyl acetal at elevated temperature, preferably at 100°–120° C.

Reaction scheme 3:

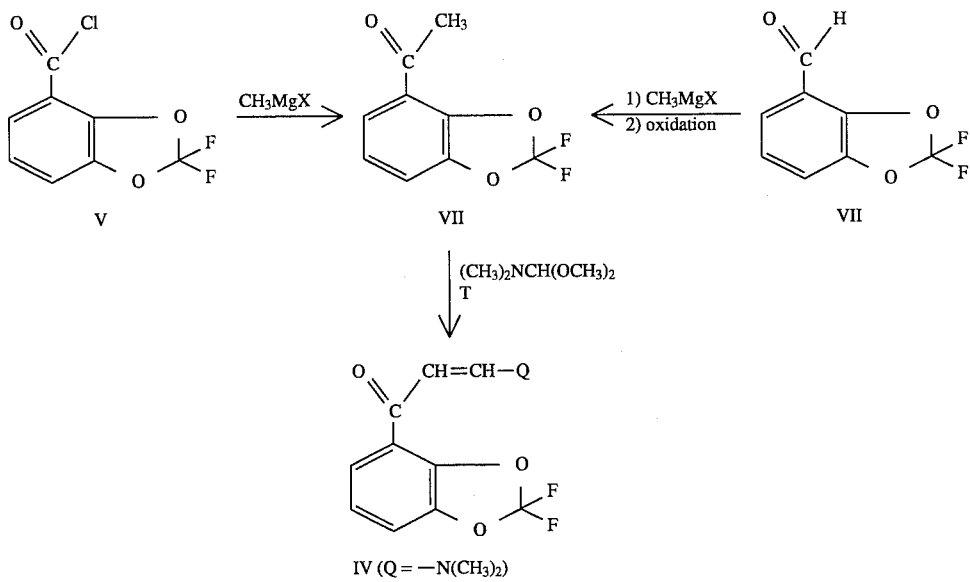

Reaction scheme 2:

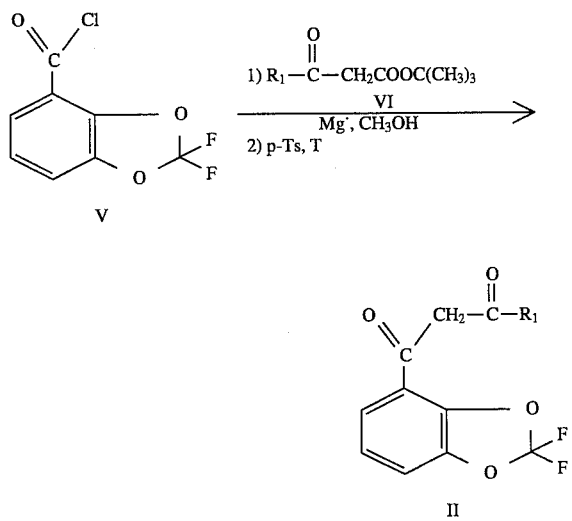

The benzoyl chloride of formula V used as starting material for the preparation of the novel intermediates of formula II (reaction scheme 2) is known and described in EP-A-0 198 797, which corresponds to U.S. Pat. No. 4,859,783.

The novel enaminoketones of formula IV can be readily prepared by different standard procedures known from the literature, as described, inter alia, in J. Org. Chem. 43, 4248

The acetophenone derivative of formula VIII can be obtained by standard procedures either from the benzoyl chloride of formula V by Grignard reaction, or from the aldehyde of formula VII by Grignard reaction and subsequent oxidation of the benzyl alcohol obtained as intermediate.

The acetophenone derivative of formula VIII is also a suitable starting material for the preparation of the 1,3-diketones of formula II (reaction scheme 2), e.g. by Claisen acylation.

The aldehyde of formula VII (reaction scheme 3) is known and described in EP-A-0 333 658, which corresponds to U.S. Pat. Nos. 5,194,628 and 5,281,718.

The 3-amino-1,2,4-triazoles of formula III are prepared as described in "The Chemistry of Heterocyclic Compounds", Volume 37, John Wiley & Sons, 1981.

The compound, 3-amino-5-trifluoromethyl-1,2,4-triazole, is known and described in Zh. Obshch. Khim. 53, 1684 (1983).

Reaction scheme 4 illustrates the diazotisation of the compound of formula Ib in aqueous-acidic solution, in the presence of the acid X-H, to prepare the compounds of formula Ic, wherein $R_1$ is as defined for formula I and X is halogen. The compounds of formula Id, wherein $R_1$, $R_3$ and Z have the given meanings, can be prepared by reacting the 2-halo-substituted triazolopyrimidine of formula Ic with the compound of formula IX

wherein M is lithium, potassium or sodium, $R_3$ is $C_1$–$C_4$alkyl, $C_1$–$C_4$haloalkyl or $C_1$–$C_4$alkoxy-$C_1$–$C_4$alkyl and Z is oxygen or sulfur.

Reaction scheme 4:

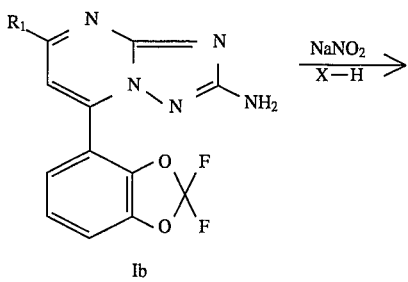

Ib

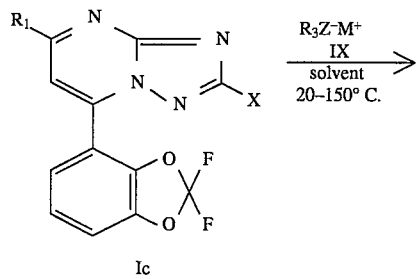

Ic

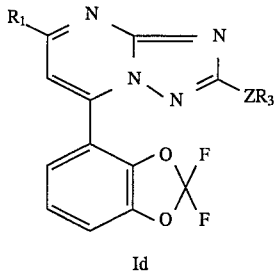

Id

Reaction scheme 5 illustrates the reaction of 2-mercapto- and 2-hydroxytriazolopyrimidines of formula Ie, wherein $R_1$ is as defined for formula I and Z is oxygen or sulfur, with the alkylating reagent of formula X $$R_3\text{-}Y \qquad (X),$$

wherein Y is a suitable leaving group such as halogen, and $R_3$ is $C_1$–$C_4$alkyl, $C_1$–$C_4$haloalkyl or $C_1$–$C_4$alkoxy-$C_1$–$C_4$alkyl, as further synthesis variant for obtaining the compounds of formula Id, wherein $R_1$, $R_3$ and Z have the given meanings.

Reaction scheme 5:

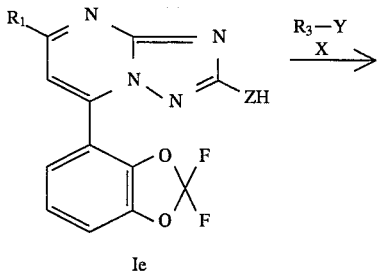

Ie

Reaction scheme 5:
-continued

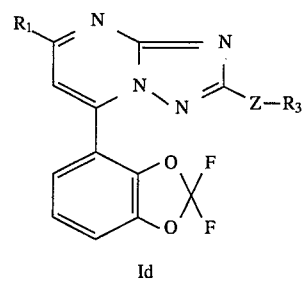

Id

The compounds of formulae Ib and Ie in reaction schemes 4 and 5 can be prepared in general accordance with the method illustrated in reaction scheme 1. In the compounds of formula III, $R_2$ is amino, hydroxyl or mercapto.

The reaction conditions for the reactions in schemes 4 and 5 are in general accordance with those described in WO 90/12012 (e.g. Preparative Examples 6 to 8 and 10 to 12).

The compounds of formula I or compositions containing them may be applied in the practice of this invention by all standard methods of application used in agriculture, including pre-emergence application, postermergence application and seed dressing, as well as by different methods and techniques, for example controlled release. For controlled release, a solution of the herbicide is applied to a mineral granular carrier or to a polymerised granulate (urea/formaldehyde) and then dried. A coating can then be additionally applied (coated granules) that allows the herbicide to be released at a controlled rate over a specific period of time.

The compounds of formula I may be used in unmodified form, i.e. as obtained in the synthesis, but preferably they are processed in conventional manner with the assistants customarily employed in formulation technology to emulsifiable concentrates, directly sprayable or dilutable solutions, dilute emulsions, wettable powders, soluble powders, dusts, granulates or microcapsules. As with the type of compositions, the methods of application such as spraying, atomising, dusting, scattering or pouring, are chosen in accordance with the intended objectives and the prevailing circumstances.

The formulations, i.e. the compositions containing the compound of formula I or at least one compound of formula I and usually one or more than one solid or liquid formulation assistant, are prepared in known manner, e.g. by homogeneously mixing and/or grinding the herbicide with said formulation assistants, typically solvents or solid carriers. Surface-active compounds (surfactants) may additionally be used for preparing the formulations.

Suitable solvents may typically be: aromatic hydrocarbons, preferably the fractions containing 8 to 12 carbon atoms such as mixtures of alkylbenzenes, typically xylene mixtures or alkylated naphthalenes; aliphatic and cycloaliphatic hydrocarbons such as paraffins, cyclohexane or tetrahydronaphthalene; alcohols such as ethanol, propanol or butanol; glycols and their ethers and esters such as propylene glycol or dipropylene glycol ether; ketones such as cyclohexanone, isophorone or diacetone alcohol; strongly polar solvents such as N-methyl-2-pyrrolidone, dimethyl sulfoxide or water;, vegetable oils and their esters such as rapeseed oil, castor oil or soybean oil; and in some cases also silicone oils.

The solid carriers typically used for dusts and dispersible powders are usually natural mineral fillers such as calcite, talcum, kaolin, montmorillonite or attapulgite. To improve the physical properties it is also possible to add highly dispersed silicic acid or highly dispersed absorbent polymers. Suitable granulated adsorptive careers are porous types, including pumice, broken brick, sepiolite or bentonite; and suitable nonsorbent carriers are materials such as calcite or sand. In addition, innumerable pregranulated materials of inorganic or organic origin may be used, especially dolomite or pulverised plant residues.

Depending on the herbicide of formula I to be formulated, suitable surface-active compounds are nonionic, cationic and/or anionic surfactants having good emulsifying, dispersing and wetting properties. Surfactants will also be understood as comprising mixtures of surfactants.

Suitable anionic surfactants may be water-soluble soaps as well as water-soluble synthetic surface-active compounds.

Suitable soaps are the alkali metal salts, alkaline earth metal salts, ammonium salts or substituted ammonium salts of higher fatty acids ($C_{10}$–$C_{22}$), e.g. the sodium or potassium salts of oleic or stearic acid, or of natural fatty acid mixtures which can be obtained, inter alia, from coconut oil or tallow oil. Further suitable soaps are also the fatty acid methyl taurin salts.

More often, however, so-called synthetic surfactants are used, especially fatty sulfonates, fatty sulfates, sulfonated benzimidazole derivatives or alkylarylsulfonates.

The fatty alcohol sulfonates or sulfates are usually in the form of alkali metal salts, alkaline earth metal salts, ammonium salts or substituted ammonium salts, and they contain a $C_8$–$C_{22}$alkyl radical which also includes the alkyl moiety of acyl radicals, e.g. the sodium or calcium salt of ligninsulfonic acid, of dodecylsulfate, or of a mixture of fatty alcohol sulfates obtained from natural fatty acids. These compounds also comprise the salts of sulfated or sulfonated fatty alcohol/ethylene oxide adducts. The sulfonated benzimidazole derivatives preferably contain two sulfonic acid groups and one fatty acid radical containing 8 to 22 carbon atoms. Illustrative examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Corresponding phosphates, typically salts of the phosphoric acid ester of an adduct of p-nonylphenol with 4 to 14 mol of ethylene oxide, or phospholipids, are also suitable.

Nonionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable nonionic surfactants are the water-soluble polyadducts of polyethylene oxide with polypropylene glycol, ethylenediaminopolypropylene glycol and alkylpolypropylene glycol containing 1 to 10 carbon atoms in the alkyl chain, which polyadducts contain 20 to 250 ethylene glycol ether groups and 10 to 100 propylene glycol ether groups. These compounds usually contain 1 to 5 ethylene glycol units per propylene glycol unit.

Illustrative examples of nonionic surfactants are nonylphenol polyethoxylates, polyethoxylated castor oil, polyadducts of polypropylene and polyethylene oxide, tributylphenol polyethoxylates, polyethylene glycol and octylphenol polyethoxylates.

Fatty acid esters of polyoxyethylene sorbitan are also suitable nonionic surfactants, typically polyoxyethylene sorbitan trioleate.

Cationic surfactants are preferably quaternary ammonium salts carrying, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl)ethylammonium bromide.

The surfactants customarily employed in the art of formulation are described, inter alia, in "Mc Cutcheon's Detergents and Emulsifiers Annual", Mc Publishing Corp., Glen Rock, N.J., 1988, H. Stache, "Tensid-Taschenbuch" (Handbook of Surfactants), Carl Hanser Verlag, Munich/Vienna 1981, and M. and J. Ash, "Encyclopedia of Surfactants", Vol I–III, Chemical Publishing Co., New York, 1980–81.

The herbicidal compositions will usually contain from 0.1 to 99% by weight, preferably from 0.1 to 95% by weight, of a compound of formula I, from 1 to 99.9% by weight of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

The compositions may also contain further ingredients such as stabilisers, vegetable oils or epoxidised vegetable oils, (epoxidised coconut oil, rapeseed oil or soybean oil), antifoams, typically silicone oil, preservatives, viscosity regulators, binders, tackifiers, as well as fertilisers or other chemical agents for obtaining special effects.

In particular, preferred formulations are made up as follows (throughout, percentages are by weight):

| Emulsifiable concentrates: | |
| --- | --- |
| herbicide: | 1 to 90%, preferably 5 to 50% |
| surfactant: | 5 to 30%, preferably 10 to 20% |
| liquid carrier: | 15 to 94%, preferably 70 to 85% |
| Dusts: | |
| herbicide: | 0.1 to 50%, preferably 0.1 to 1% |
| solid carrier: | 99.9 to 90%, preferably 99.9 to 99% |
| Suspension concentrate: | |
| herbicide: | 5 to 75%, preferably 10 to 50% |
| water | 94 to 24%, preferably 88 to 30% |
| surfactant: | 1 to 40%, preferably 2 to 30% |
| Wettable powder: | |
| herbicide: | 0.5 to 90%, preferably 1 to 80% |
| surfactant: | 0.5 to 20%, preferably 1 to 15% |
| solid carrier: | 5 to 95%, preferably 15 to 90% |
| Granulate: | |
| herbicide | 0.1 to 30%, preferably 0.1 to 15% |
| solid carrier: | 99.5 to 70%, preferably 97 to 85% |

The compounds of formula I are usually applied with success to the plants or the locus thereof in concentrations of 0.001 to 2 kg/ha, preferably 0.005 to 1 kg/ha. The concentration required to achieve the desired action can be determined by experimentation. It will depend on the type of action, the development stage of the cultivated plant and of the weed, as well as on the application (locus, time, method) and, based on these parameters, can vary over a wide range.

The compounds of formula I have excellent growth inhibiting and herbicidal properties, which make them pre-eminently suitable for application in crops of cultivated plants.

Crops will also be understood as meaning those crops that have been made tolerant to herbicides or classes of herbicides by conventional breeding or genetic engineering methods.

The invention is illustrated in more detail by the following non-limitative Examples.

Preparative Examples

Example P1: Preparation of (2,3-difluoromethylenedioxy)benzoyl acetone (intermediate)

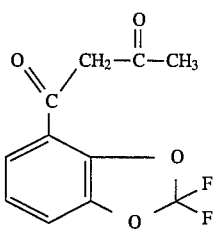

To 700 ml of methanol and 1 ml of carbon tetrachloride are added, in increments, 24.3 g of magnesium turnings. The reaction mixture is kept at 40° C. by cooling. All the magnesium has dissolved after 3 hours. Then 173.8 g of tert-butyl acetoacetate are added dropwise over 30 minutes. After the exothermic reaction has subsided, the solvent is stripped off on a rotary evaporator and the white residue is dried at 40° C. under a high vacuum. Then 1000 ml of diethyl ether are added and 220.5 g of 2,3-difluoromethylenedioxybenzoyl chloride are added dropwise to the resultant suspension over 1 hour. The reaction mixture is then refluxed for 2 hours, poured on to a mixture of ice-water/hydrochloric acid and extracted with toluene. The combined toluene phases are dried over sodium sulfate and, after addition of 2.0 g of p-toluenesulfonic acid, refluxed for 8 hours. The cooled reaction mixture is poured on to a mixture of ice-water and the precipitate is isolated by filtration and dried, giving 185.9 g of (2,3-difluoromethylenedioxy)benzoyl acetone.

The separated toluene phase is dried over sodium sulfate and concentrated to give a further 39.8 g of the desired intermediate (total yield: 225.7 g) with a melting point of 92°–94° C.

Example P2: Preparation of 5-methyl-2-trifluoromethyl-7-(2,3-difluoromethylenedioxyphenyl)-1,2,4-triazolo[1,5-a]pyrimidine

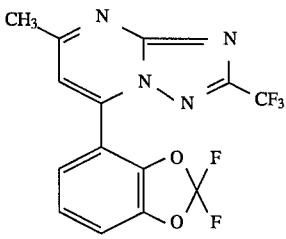

(1.018)

9.6 g of (2,3-difluoromethylenedioxy)benzoyl acetone and 9.1 g of 3-amino-5-trifluoromethyl-1, 2,4-triazole are refluxed in 60 ml of glacial acetic acid for 5 hours. The reaction mixture is concentrated on a rotary evaporator, and the residue is taken up in diethyl ether and washed twice with water. The ether phase is dried over sodium sulfate and concentrated. The residue is chromatographed on a column of silica gel with ethyl acetate/hexane 1:2 as eluant, giving 12.3 g of 5-methyl-2-trifluoromethyl-7-(2, 3-difluoromethylenedioxyphenyl)-1,2,4-triazolo[1,5-a]pyrimidine with a melting point of 145°–146° C.

The compounds listed in the following Table can be prepared in analogous manner.

TABLE 1

Compounds of formula I

| Cmpd. No. | $R_1$ | $R_2$ | Physical data |
|---|---|---|---|
| 1.001 | $CH_3$ | $SCH_3$ | m.p. 149–150° C. |
| 1.002 | $CH_3$ | $SCF_3$ | |
| 1.003 | $CH_3$ | $CF_2Cl$ | |
| 1.004 | $CH_3$ | $CHF_2$ | m.p. 138–143° C. |
| 1.005 | $CH_3$ | Cl | m.p. 164–166° C. |
| 1.006 | $CH_3$ | Br | m.p. 157–159° C. |
| 1.007 | $CH_3$ | $SCHF_2$ | m.p. 147–148° C. |
| 1.008 | $CH_3$ | $C_2F_5$ | m.p. 121–123° C. |
| 1.009 | $CH_3$ | $CCl_2CF_3$ | |
| 1.010 | $CH_3$ | $OCH_3$ | m.p. 138–140° C. |
| 1.011 | $CH_3$ | $OCHF_2$ | m.p. 137–138° C. |
| 1.012 | $CH_3$ | $OCH_2CF_3$ | m.p. 125–129° C. |
| 1.013 | $CH_3$ | $OCF_2CHF_2$ | |
| 1.014 | $CH_3$ | $OCH_2OCH_3$ | |
| 1.015 | $CH_3$ | $NH_2$ | m.p. 238–240° C. |
| 1.016 | $CH_3$ | $NHCH_3$ | m.p. 184–186° C. |
| 1.017 | $CH_3$ | $N(CH_3)_2$ | |
| 1.018 | $CH_3$ | $CF_3$ | m.p. 145–146° C. |
| 1.019 | H | $OCHF_2$ | |
| 1.020 | H | $CH_3$ | |
| 1.021 | $CF_3$ | $CF_3$ | |
| 1.022 | $C_2H_5$ | $CF_3$ | |
| 1.023 | $C_2H_5$ | $OCHF_2$ | |
| 1.024 | $C_2H_5$ | $OCH_2CF_3$ | |
| 1.025 | H | $CF_3$ | m.p. 122–123° C. |
| 1.026 | $CH_3$ | CHFCl | m.p. 139–141° C. |
| 1.027 | $CH_3$ | $OC_2H_5$ | m.p. 138–140° C. |
| 1.028 | $CH_3$ | $OC_3H_7(i)$ | m.p. 176–177° C. |

Formulation Examples for herbicides of formula I (throughout, percentages are by weight)

| F1. Emulsifiable concentrates | a) | b) | c) | d) |
|---|---|---|---|---|
| compound of Table 1 | 5% | 10% | 25% | 50% |
| calcium dodecylbenzenesulfonate | 6% | 8% | 6% | 8% |
| polyethoxylated castor oil (36 mol EO) | 4% | — | 4% | 4% |
| octylphenol polyethoxylate (7–8 mol EO) | — | 4% | — | 2% |
| cyclohexanone | — | — | 10% | 20% |
| mixture of aromatic hydrocarbons $C_9$–$C_{12}$ | 85% | 78% | 55% | 16% |

Emulsions of any desired concentration can be prepared by diluting such concentrates with water.

| F2. Solutions | a) | b) | c) | d) |
|---|---|---|---|---|
| compound of Table 1 | 5% | 10% | 50% | 90% |
| 1-methoxy-3-(3-methoxypropoxy)-propane | — | 20% | 20% | — |
| polyethylene glycol 400 | 20% | 10% | — | — |
| N-methyl-2-pyrrolidone | — | — | 30% | 10% |
| mixture of aromatic hydrocarbons | 75% | 60% | — | — |

-continued

| F2. Solutions | a) | b) | c) | d) |
|---|---|---|---|---|
| $C_9$–$C_{12}$ | | | | |

The solutions are suitable for use as microdrops.

| F3. Wettable powders | a) | b) | c) | d) |
|---|---|---|---|---|
| compound of Table 1 | 5% | 25% | 50% | 80% |
| sodium ligninsulfonate | 4% | — | 3% | — |
| sodium laurylsulfate | 2% | 3% | — | 4% |
| sodium diisobutylnaphthalene sulfonate | — | 6% | 5% | 6% |
| octylphenol polyethoxylate (7–8 mol EO) | — | 1% | 2% | — |
| highly dispersed silica | 1% | 3% | 5% | 10% |
| kaolin | 88% | 62% | 35% | — |

The compound is throughly mixed with the adjuvants and this mixture is ground in a suitable mill to give wettable powders which can be diluted with water to give suspensions of any desired concentration.

| F4. Coated granulates | a) | b) | c) |
|---|---|---|---|
| compound of Table 1 | 0.1% | 5% | 15% |
| highly dispersed silica | 0.9% | 2% | 2% |
| inorganic carrier (Ø 0.1–1 mm) e.g. $CaCO_3$ or $SiO_2$ | 99.0% | 93% | 83% |

The compound is dissolved in methylene chloride, the solution is sprayed on to the carrier, and the solvent is removed under vacuum.

| F5. Coated granulates | a) | b) | c) |
|---|---|---|---|
| compound of the Table 1 | 0.1% | 5% | 15% |
| polyethylene glycol MW 200 | 1.0% | 2% | 3% |
| highly dispersed silica | 0.9% | 1% | 2% |
| inorganic carrier (Ø 0.1–1 mm) e.g. $CaCO_3$ or $SiO_2$ | 98.0% | 92% | 80% |

The finely ground compound is uniformly applied in a mixer to the kaolin moistened with polyethylene glycol. Non-dusty coated granulates are obtained in this manner.

| F6. Extruder granulates | a) | b) | c) | d) |
|---|---|---|---|---|
| compound of the Table 1 | 0.1% | 3% | 5% | 15% |
| sodium ligninsulfonate | 1.5% | 2% | 3% | 4% |
| carboxymethyl cellulose | 1.4% | 2% | 2% | 2% |
| kaolin | 97.0% | 93% | 90% | 79% |

The compound is mixed with the adjuvants and the mixture is moistened with water. This mixture is extruded and then dried in a stream of air.

| F7. Dusts | a) | b) | c) |
|---|---|---|---|
| compound of Table 1 | 0.1% | 1% | 5% |
| talcum | 39.9% | 49% | 35% |
| kaolin | 60.0% | 50% | 60% |

Ready for use dusts are obtained by mixing the active ingredient with the carriers on a suitable mill.

| F8. Suspension concentrates | a) | b) | c) | d) |
|---|---|---|---|---|
| compound of Table 1 | 3% | 10% | 25% | 50% |
| ethylene glycol | 5% | 5% | 5% | 5% |
| nonylphenol polyethoxylate (15 mol EO) | — | 1% | 2% | — |
| sodium ligninsulfonate | 3% | 3% | 4% | 5% |
| carboxymethyl cellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground compound mixture is intimately mixed with the adjuvants to give a suspension concentrate from which suspensions of any desired concentration can be prepared by dilution with water.

Biological Examples

Example B1: Pre-emergence herbicidal action

Monocot and dicot test plants are sown in standard soil in plastic pots. Immediately after sowing, the plants are sprayed with an aqueous suspension of the test compound prepared from a 25% wettable powder formulation (Example F3b) at a concentration of 2 kg a.i./ha (500 l of water/ha). The test plants are thereafter cultivated in a greenhouse under optimum conditions. The test is evaluated 3 weeks later using a scale with a rating of 1–9 (1=total damage, 9=no action). Ratings of 1 to 4 (especially of 1 to 3) denote good to very good herbicidal action.

TABLE B1

Pre-emergence action:

| | Test plant: | | | |
|---|---|---|---|---|
| Compound No. | Avena | Setaria | Sinapis | Stellaria |
| 1.001 | 1 | 2 | 2 | 1 |
| 1.004 | 1 | 1 | 1 | 1 |
| 1.005 | 1 | 1 | 1 | 1 |
| 1.006 | 1 | 1 | 1 | 1 |
| 1.007 | 1 | 1 | 1 | 1 |
| 1.008 | 1 | 1 | 1 | 1 |
| 1.011 | 1 | 1 | 1 | 1 |
| 1.012 | 1 | 1 | 1 | 1 |
| 1.016 | 2 | 2 | 3 | 1 |
| 1.018 | 1 | 1 | 1 | 1 |
| 1.025 | 1 | 1 | 1 | 1 |

The same results are obtained by formulating the compounds of formula I in accordance with Examples F1, F2 and F4 to F8.

Example B2: Postemergence herbicidal action (contact herbicide).

A number of weeds, monocots as well as dicots, are sprayed postemergence in the 4- to 6-leaf stage with an aqueous dispersion of the test compound prepared according to Example F3b) at a concentration of 8–500 g a.i./ha. Afterwards the test plants are further cultivated in a greenhouse under optimum conditions.

The herbicidal action is evaluated 3 weeks later using a scale with a rating of 1–9 (1=total damage, 9=no action) in comparison with an untreated control group. Ratings of 1 to 4 (especially of 1 to 3) denote good to very good herbicidal action. Ratings of 6 to 9 (especially of 7 to 9) indicate good tolerance (especially by cultivated plants).

TABLE B2

| | Postemergence action: | | | |
|---|---|---|---|---|
| | Test plant: | | | |
| Compound No. | Avena | Setaria | Sinapis | Stellaria |
| 1.004 | 2 | 1 | 1 | 2 |
| 1.005 | 3 | 2 | 2 | 2 |
| 1.007 | 2 | 3 | 1 | 2 |
| 1.008 | 2 | 2 | 1 | 2 |
| 1.011 | 2 | 2 | 1 | 2 |
| 1.912 | 2 | 2 | 1 | 2 |
| 1.018 | 1 | 2 | 1 | 2 |
| 1.025 | 2 | 4 | 1 | 2 |

The same results are obtained by formulating the compounds of formula I in accordance with Examples F1, F2 and F4 to F8.

What is claimed is:

1. A compound of formula

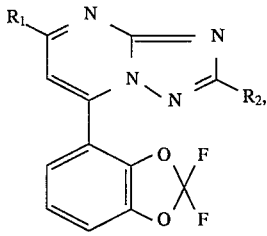

(I)

wherein $R_1$ is hydrogen, $C_1$–$C_4$alkyl or $C_1$–$C_4$haloalkyl; and $R_2$ is $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkoxy-$C_1$–$C_4$alkyl, $C_1$–$C_4$alkoxy-$C_1$–$C_4$alkoxy, $C_1$–$C_4$alkoxy-$C_1$–$C_4$alkylthio, halogen, amino, $C_1$–$C_4$alkylamino or $C_1$–$C_4$dialkylamino.

2. A compound according to claim 1, wherein $R_1$ is hydrogen or $C_1$–$C_4$alkyl.

3. A compound according to claim 2, wherein $R_1$ is hydrogen, methyl or ethyl.

4. A compound of formula I according to claim 1, wherein $R_1$ is methyl and $R_2$ has the given meaning.

5. A compound according to claim 4, wherein $R_2$ is trifluoromethyl or $C_1$–$C_4$haloalkoxy.

6. A compound according to claim 1, wherein $R_2$ is $C_1$–$C_4$alkyl, $C_1$–$C_4$haloalkyl, $C_1$–$C_4$alkoxy, $C_1$–$C_4$haloalkoxy, halogen, amino, $C_1$–$C_4$alkylamino or $C_1$–$C_4$dialkylamino.

7. A compound according to claim 6, wherein $R_2$ is $C_1$–$C_2$alkyl, $C_1$–$C_2$haloalkyl, $C_1$–$C_2$alkoxy, $C_1$–$C_2$haloalkoxy, chloro, bromo, amino, methylamino or dimethylamino.

8. A compound according to claim 7, wherein $R_2$ is $C_1$–$C_2$haloalkyl, $C_1$–$C_2$haloalkoxy or amino.

9. A compound according to claim 1, wherein $R_2$ is $C_1$–$C_4$alkylthio, $C_1$–$C_4$haloalkylthio or $C_1$–$C_4$alkoxy-$C_1$–$C_4$alkoxy.

10. A compound according to claim 9, wherein $R_2$ is $C_1$–$C_2$alkylthio, $C_1$–$C_2$haloalkylthio or $C_1$–$C_2$alkoxy-$C_1$–$C_2$alkoxy.

11. A compound according to claim 1, wherein $R_1$ is hydrogen, $C_1$–$C_2$alkyl or trifluoromethyl; and $R_2$ is $C_1$–$C_2$haloalkyl, $C_1$–$C_2$haloalkoxy or amino.

12. A compound according to claim 11, wherein $R_2$ is trifluoromethyl or $C_1$–$C_4$haloalkoxy.

13. A compound according to claim 1, wherein $R_1$ is hydrogen, methyl, ethyl or trifluormethyl; and $R_2$ is methyl, methoxy, methoxymethoxy, chloro, bromo, trifluoromethyl, difluoromethyl, chlorodifluoromethyl, pentafluoroethyl, 1,1-dichloro- 2,2,2-trifluoroethyl, difluoromethoxy, 2,2,2-trifluoroethoxy, 1,1,2,2-tetrafluoroethoxy, methylthio, difluoromethylthio, trifluoromethylthio, amino, methylamino or dimethylamino.

14. A compound of formula II

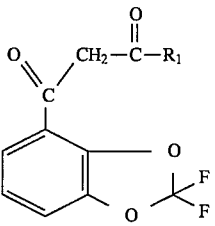

(II)

wherein $R_1$ is $C_1$–$C_4$alkyl or $C_1$–$C_4$haloalkyl.

15. A compound of formula IV

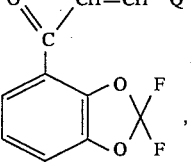

(IV)

wherein Q is a leaving group.

16. A herbicidal and plant growth inhibiting composition, which comprises one or more than one compound of formula I as claimed in claim 1.

17. A composition according to claim 16, which comprises from 0.1 to 95% by weight of a compound of formula I, from 1 to 99.9% by weight of a solid or liquid adjuvant and from 0 to 25%, preferably from 0.1 to 25%, of a surfactant.

18. A method of controlling undesirable plant growth, which comprises treating said plants or the locus thereof with a herbicidally effective amount of a compound of formula I as claimed in claim 1 or of a composition containing such a compound.

19. A method according to claim 18, which comprises applying a compound of formula I in a concentration in the range from 0.001 to 2 kg per hectare.

20. A method according to claim 18 for selectively controlling weeds pre- or postemergence in crops of cultivated plants.

* * * * *